US009436985B1

(12) United States Patent
Kuan et al.

(10) Patent No.: US 9,436,985 B1
(45) Date of Patent: *Sep. 6, 2016

(54) METHOD AND SYSTEM FOR ENHANCING IMAGE QUALITY

(71) Applicant: Hermes Microvision Inc., Hsinchu (TW)

(72) Inventors: Chiyan Kuan, Danville, CA (US); Joe Wang, Campbell, CA (US); Van-Duc Nguyen, Pleasanton, CA (US)

(73) Assignee: HERMES MICROVISION INC., Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/595,582

(22) Filed: Jan. 13, 2015

Related U.S. Application Data

(63) Continuation of application No. 13/776,939, filed on Feb. 26, 2013, now Pat. No. 9,002,097.

(51) Int. Cl.
*G06K 9/00* (2006.01)
*G06K 9/54* (2006.01)
*G06T 5/50* (2006.01)
*G06T 5/40* (2006.01)

(52) U.S. Cl.
CPC . *G06T 5/50* (2013.01); *G06T 5/40* (2013.01); *G06T 2207/20172* (2013.01); *G06T 2207/20216* (2013.01); *G06T 2207/30148* (2013.01)

(58) Field of Classification Search
CPC ......... G06K 9/40; G03F 7/7065; G03F 1/86; G01N 2223/42; G01N 2223/6116; G01N 2223/2251; G06T 2207/30148; H01J 37/28
USPC .......................................... 382/145, 149, 254
See application file for complete search history.

(56) References Cited

U.S. PATENT DOCUMENTS

| 6,169,282 | B1 | 1/2001 | Maeda et al. |
| 6,545,275 | B1* | 4/2003 | Pearl ........................ H01J 37/28 250/307 |
| 7,831,083 | B1 | 11/2010 | Lauber |
| 8,068,662 | B2 | 11/2011 | Zhang et al. |
| 8,582,864 | B2 | 11/2013 | Maeda et al. |
| 8,606,017 | B1 | 12/2013 | Fang et al. |
| 2005/0012050 | A1* | 1/2005 | Shemesh ............. H01J 37/1471 250/491.1 |
| 2006/0022295 | A1* | 2/2006 | Takafuji .................. H01L 22/14 257/495 |
| 2010/0158317 | A1 | 6/2010 | Fang et al. |
| 2011/0036981 | A1* | 2/2011 | Zhao ................... G01N 23/2206 250/307 |

* cited by examiner

*Primary Examiner* — Kanjibhai Patel
(74) *Attorney, Agent, or Firm* — WPAT, PC; Justin King; Douglas Hosack

(57) ABSTRACT

This invention relates to methods and systems for enhance the signal-to-noise ratio of an image scanned by a charged particle beam. In an embodiment, a sequence of grayscales of a pixel is recorded first, extreme values of the sequence of grayscales are then identified and removed, and the remained grayscales are used to determine a nominated grayscale of the pixel.

26 Claims, 7 Drawing Sheets

A,B,C,D respectively denotes discarded grayscales scanned at T=1,T=2,T=3,and T=4

METHOD AND SYSTEM FOR ENHANCING IMAGE QUALITY

CROSS REFERENCE TO RELATED APPLICATIONS

This application is a continuation application of application Ser. No. 13/776,939, filed Feb. 26, 2013 and entitled "METHOD AND SYSTEM FOR ENHANCING IMAGE QUALITY," the entire contents of the foregoing application are incorporated herein by reference.

BACKGROUND OF THE INVENTION

1. Field of the Invention

The present invention relates to a method for enhancing image quality scanned by using an inspection tool.

2. Description of Related Art

During the fabrication of semiconductor, pattern defects occur on the mask or wafer reducing the yield to a great degree. Defect inspection and review are widely used for yield management. High resolution, high throughput, and low radiation damage on specimen are requested for defect inspection systems.

Defect inspection systems frequently utilize charged particle beams. In such systems, a charged particle beam, such as an electron beam (e-beam), is irradiated on structures to be inspected. The interaction of the electron beam with the inspected surface generates secondary electron signals, which is collected as grayscale images, and which are compared to detect defect by observing the change in gray scale.

As the dimensions of structures to be inspected are continuously getting smaller and the resolution of the inspection systems are getting higher, enormous amount of data are generated. In addition, because the secondary electron signals may be strongly affected by extremely irregular noise, the e-beam inspection typically use multi-scans, i.e., repeated scans, for a same sample to obtain low noise image.

After multi-scans, all scanned grayscales of each pixel are averaged, and a scanned image with low noise is thus obtained.

Theoretically, the more times of the scan have been made, the better image quality would be; however, the e-beam inspection is a time-consuming process, and the increased complexity of structures and times of scan increase the cost of defect inspections, both in terms of expense and time.

The scan times may be reduced or limited to lower the cost, but image quality would be a critical concern. Deteriorated image quality may ignore small defect and increase the false rate on defect determination, causes alignment error in the following alignment process, and even result in the devices to fail. As the dimensions of semiconductor devices decrease, inspection becomes even more important and image quality should be promoted.

Median filter is a nonlinear digital filtering technique used to remove noise. The main idea of the median filter is to run through the signal entry by entry, replacing each entry with the median of neighboring entries. In one image frame, a pixel with its neighbor can form a matrix, and a median value can be determined from this matrix to replace the possible extreme value of this pixel.

The median filter is not suitable for the defect inspection systems. If a defect happens to one pixel only, this defect will be ignored by the median filter. In addition, larger image distortion occurs when tuning brightness and contrast.

In short, scan times should be reasonably reduced for saving time and cost. In limited scan times, the image quality has to be promoted, but qualified images are not always provided through a traditional averaging or median filter method. Therefore, it would be advantageous to provide methods or systems for enhancing the image quality.

SUMMARY OF THE INVENTION

An object of this invention is to provide methods or systems for enhancing the image quality, thereby saving time and cost.

An embodiment of this invention provides a method for enhancing image quality, comprising the steps of: recording a sequence of grayscales of a pixel scanned by a charged particle beam; removing extreme values from the sequence of grayscales and remaining other grayscales; and determining a nominated grey level of the pixel from the remained grayscales.

Another embodiment of this invention provides a system for enhancing image quality, comprising: means for recording a sequence of grayscales of a pixel scanned by a charged particle beam; means for removing extreme values from the sequence of grayscales and remaining other grayscales; and means for calculating an average or a median of the remained grayscales to obtain an nominated grayscale of the pixel.

Another embodiment of this invention provides a method for enhancing image quality, comprising: scanning a specimen to obtain a plurality of frames by using a charged particle beam; removing extreme grayscales of each pixel of the plurality of frames; and averaging remained grayscales of each pixel of the plurality of frames to obtain a scanned image of the specimen.

DESCRIPTION OF THE PREFERRED EMBODIMENT

Figure 1:
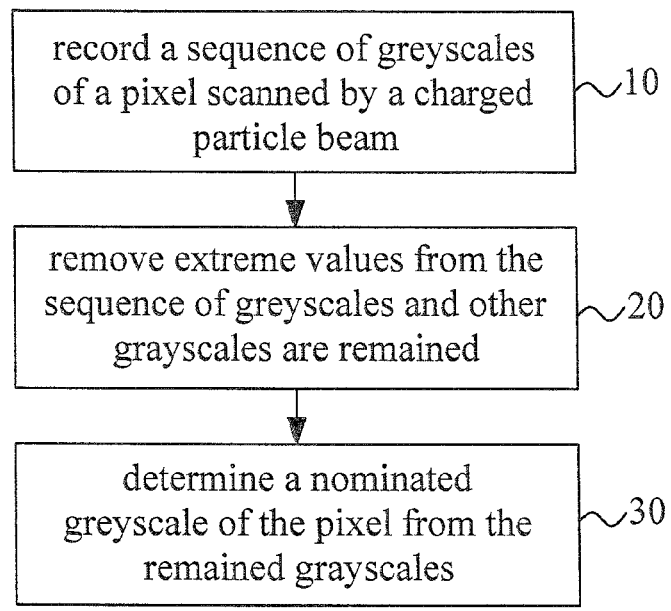
FIG. 1 shows a method for enhancing image contrast according to an embodiment of this invention.

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known components and process operations have not been described in detail in order not to unnecessarily obscure the present invention. While drawings are illustrated in detail, it is appreciated that the quantity of the disclosed components may be greater or less than that disclosed, except where expressly restricting the amount of the components.

This invention is directed to methods and systems for improving image quality of frames obtained from an inspection system. The inspection system repeatedly inspects a sample, and the inspected frames for the same sample are processed to obtain an improved image. Preferably, a cherry-pick method is employed to remove noises or values of the frames. The term "cherry-pick" refers to employing an automatic or manual way, or an arbitrary or rational rule, to pick out the unwanted noises or values.

The inspection system may be an optical inspection system, or an inspection system using a charged particle beam. Preferably, embodiments of this invention employ the cherry-pick method to treat frames obtained from insufficient quantity of inspection times. For frames obtained from many inspection times, e.g., 100 times, the cherry-pick method may be unnecessary because the noises may contribute little weight in such cases. Preferably, the cherry-pick method is employed to treat frames obtained from limited inspection times, e.g., 4 or 10 times. Noises contribute big weight in such cases and they have to be removed.

Preferably, the inspection system uses a charged particle beam to inspect the sample. Systems capable of irradiating a charged particle beam can be employed by this invention. The charged particle beam interacts with the sample and signals are thus generated and collected as grayscale frames. The inspection system using the charged particle beam has the advantage of high resolution.

Typically, the inspection system is a point-to-point imaging system, such as a scanning electron microscope (SEM), a focused ion beam (FIB), or an atomic force microscope (AFM) inspection system. Scanning electron microscope (SEM) is an electron microscope that images a sample by scanning it with a high-energy beam of electrons in a raster scan pattern. The electrons of the beam interact with the atoms that make up the sample producing signals that contain information about the sample's surface topography. The focused ion beam resembles the SEM, the focused ion beam uses a focused beam of ions instead of a focused beam of electrons. The atomic force microscope was developed to overcome drawbacks of STM. AFM is capable of imaging almost any type of surfaces.

Figure 2:
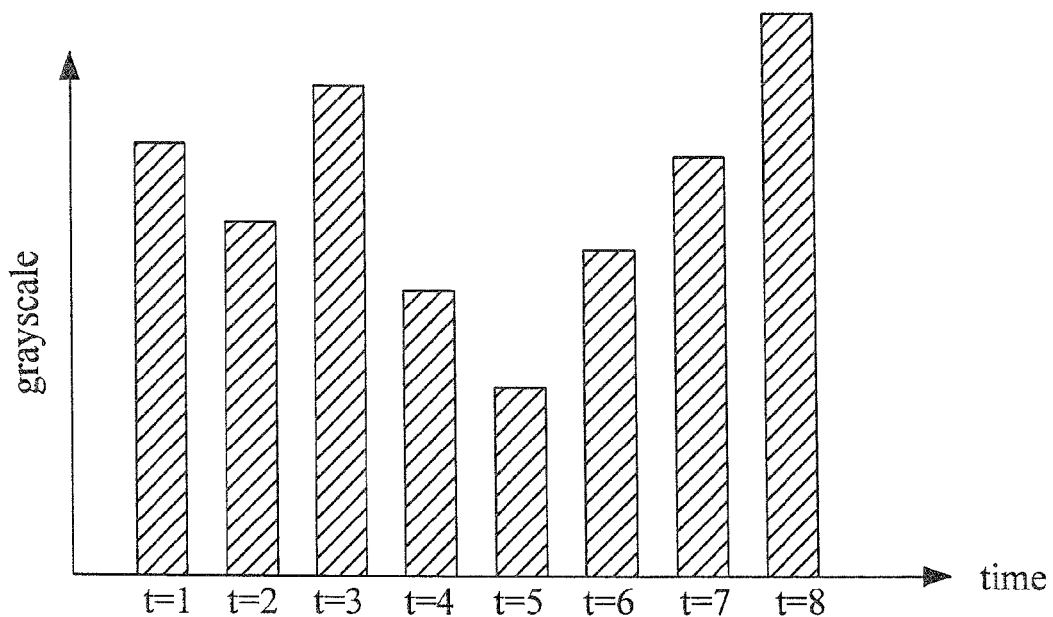
FIG. 2 shows recorded eight scanned grayscales with time information of a particular pixel.

FIG. 1 shows a method for enhancing image quality according to an embodiment of this invention. Step 10, a sequence of grayscales of a pixel scanned by a charged particle beam is recorded. Preferably, the method may employ a defect invention system emitting electron beams to repeatedly scan a specimen in time sequence. The specimen may comprise a wafer, such as a silicon wafer, or a mask, such as an extreme ultraviolet mask. The times of multi-scan may range from several to tens. For example, a 12 inch wafer is scanned for 8 times and eight frames are obtain, in which grayscales of each pixel of each frame incorporated with time information are recorded. FIG. 2 shows the recorded eight scanned grayscales with time information of a particular pixel.

Referring to FIG. 1 again, in step 20, some of the recorded grayscales are removed from the sequence, and other grayscales are remained. The method of this invention may employ a statistic manner to remove extreme values from the recorded sequence of grayscales. The recorded grayscales may be firstly analyzed to identify its distribution by statistic charts, such as histogram, or other methods know in the art.

Figure 3A:
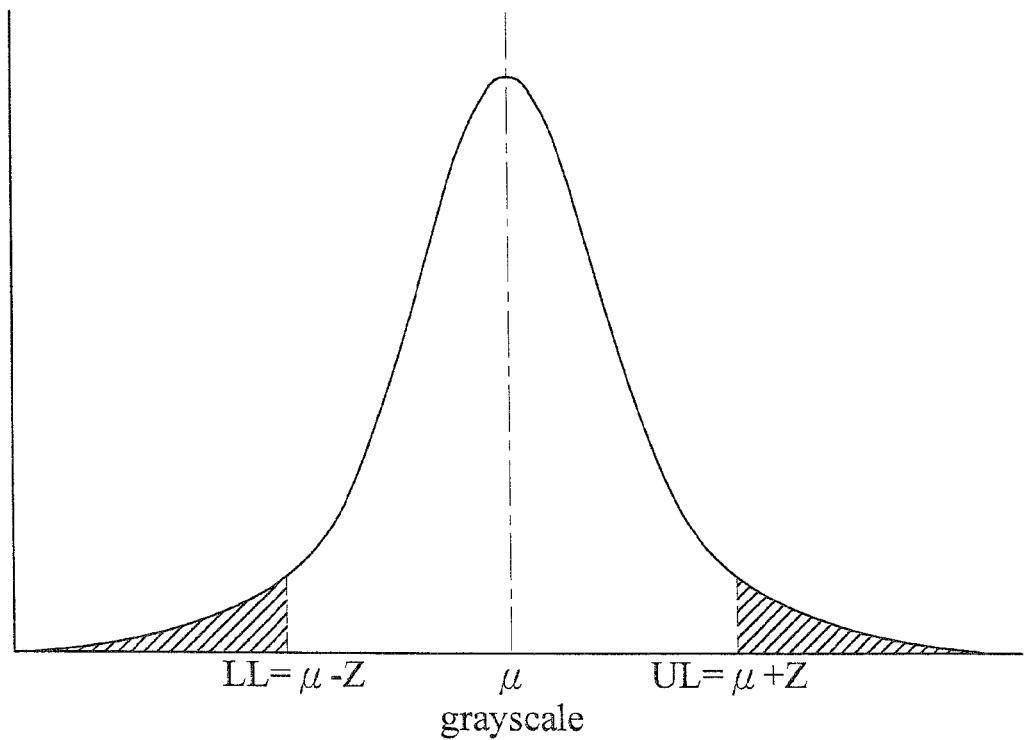
FIG. 3A shows an example for discarding the extreme grayscales.
Figure 3B:
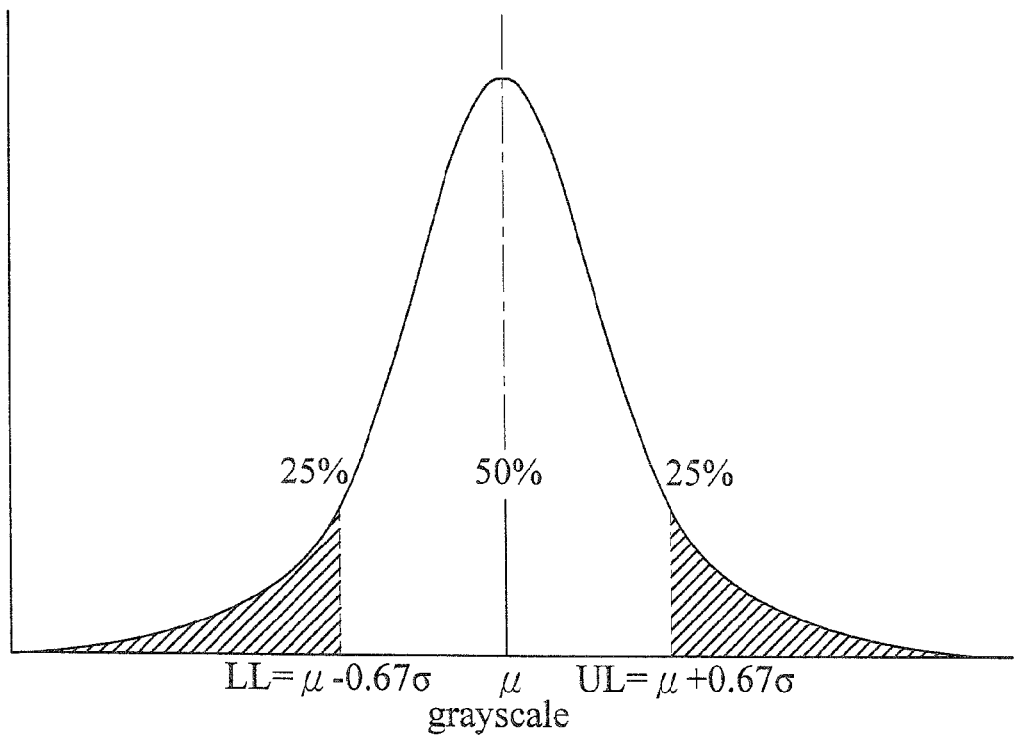
FIG. 3B shows a particular example of FIG. 3A.
Figure 3C:
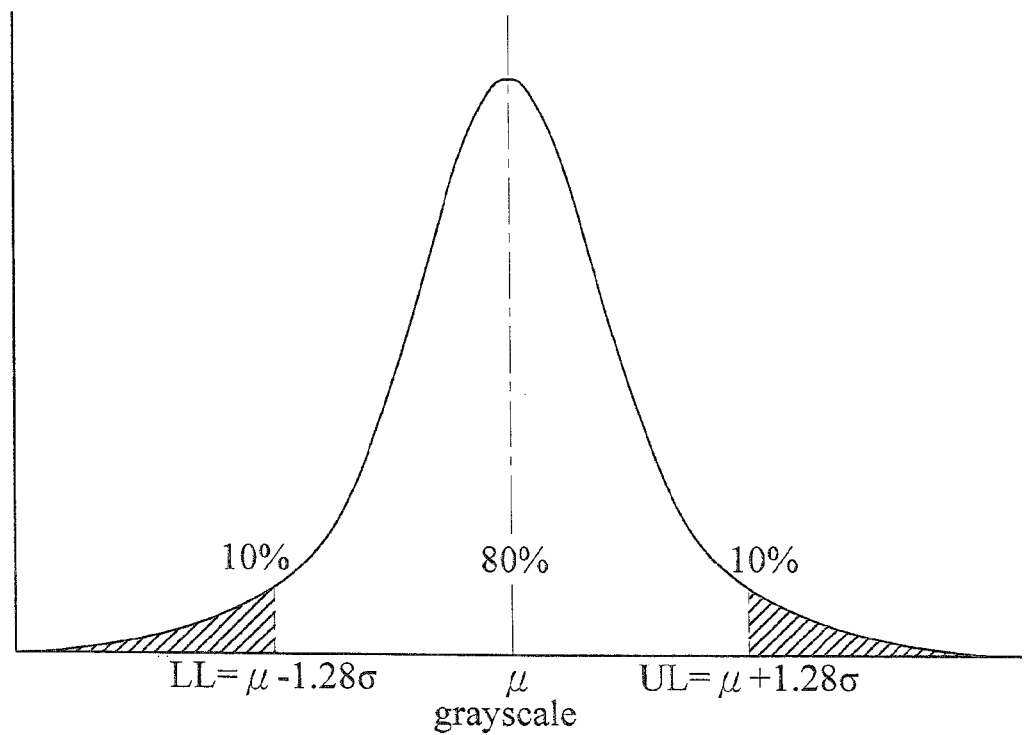
FIG. 3C shows another particular example of FIG. 3A.

If the distribution is a standard normal distribution, an upper limit and a lower limit may be defined to remove the abnormal extreme values. The extreme grayscales may be due to the apparatus for emitting the charged particle beam, or due to accumulated charge in the scanned surface. FIG. 3A shows an example for discarding the extreme grayscales. The distribution of the recorded grayscales is a standard normal distribution with a mean $\mu$ and a standard deviation $\sigma$. An upper limit (UL) and a lower limit (LL) are respectively defined as UL=$\mu$+z, and LL=$\mu$-z, where z stands for a predetermined value multiplied the standard deviation ($\sigma$) of the normal distribution, usually ranged from about 0.5 $\sigma$ to about 3$\sigma$. Grayscales greater than the upper limit and smaller than the lower limit will be discarded and others are remained. FIG. 3B shows a particular example of FIG. 3A in which the upper limit UL and the lower limit LL are respectively defined as UL=$\mu$+0.67$\sigma$, and LL=$\mu$-0.67$\sigma$. In this example, the area under the normal curve within 0.67 standard deviation of the mean is about 50% of the total area under the curve. FIG. 3C shows another particular example of FIG. 3A in which the upper limit UL and the lower limit LL are respectively defined as UL=$\mu$+1.28$\sigma$, and LL=$\mu$-1.28$\sigma$. In this example, the area under the normal curve within 1.28 standard deviation of the mean is about 80% of the total area under the curve.

Notice that some embodiments of this invention may use only the upper limit UL or the lower limit LL to discard extreme grayscales. In addition, if the number of scans are too small or the distribution is not normal distribution, it may use other definitions to discard the grayscales caused by noise. In one embodiment, the extreme values are defined as the highest 25% and lowest 25% of the recorded sequence of grayscales. For example, the specimen is repeatedly scanned for four times and each pixel has four grayscales. According to the definition, the maximum and the minimum of the four will be discarded. In another embodiment, the extreme values are defined as the highest 10% and lowest 10% of the recorded sequence of grayscales.

In addition, some embodiment cherry-picks the recorded sequence of grayscales, picking up grayscales only within suitable range regardless whatever distributions.

Figure 4:
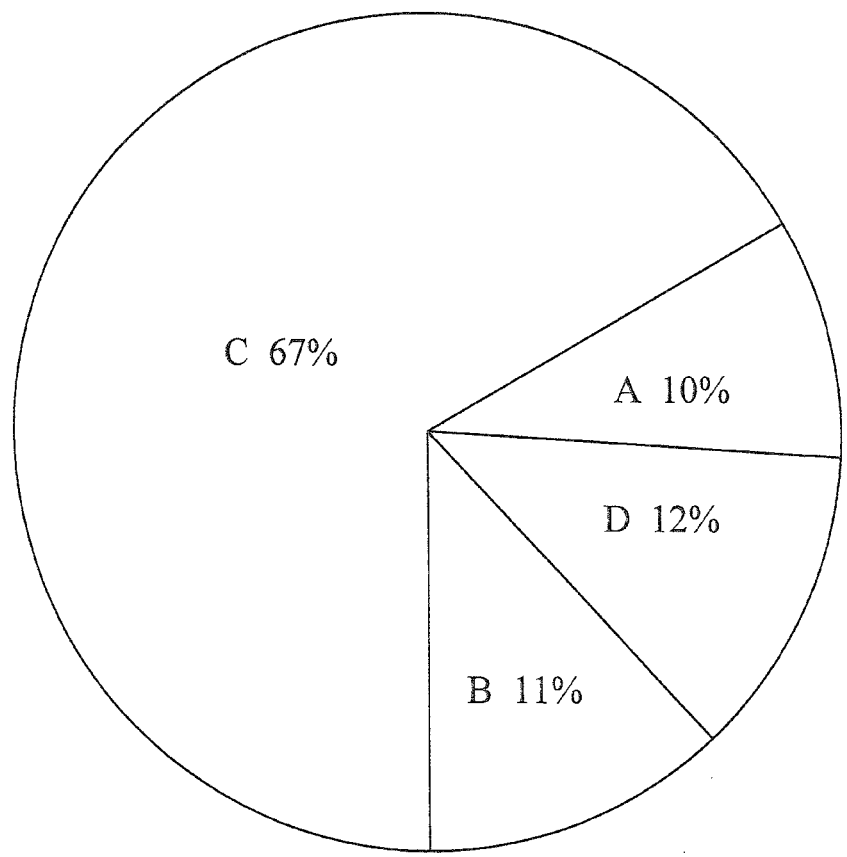
FIG. 4 shows an example in which a pie chart is used to check whether the discarded grayscales correlate with the time of scan.

An error diagnose may be made before removing the extreme grayscales and the extreme values may be accordingly defined. The recorded sequence of grayscales incorporated with time information, as well as the parameters of scans, may provide useful information to spot the source of the noise. The diagnose may use various statistical charts. FIG. 4 shows an example in which a pie chart is used to check whether the discarded grayscales correlate with the time of scan. The symbol A, B, C, and D respectively denote the discarded grayscales scanned at T=1, T=2, T=3, and T=4 for a four-times scan. The probability of each scan should be almost the same and about 25% in theory. The pie chart, however, tells that 67% the discarded grayscales are scanned at T=3, and some special cause, such as electrons accumulated in the specimen surface, may disturb the probability distribution. In this case, all grayscales scanned at T=3 may be discarded.

The definition of extreme grayscales may be changed after the error diagnose. For example, in the four-times scan shown in the last paragraph, it is diagnosed that the grayscales are deviated to high due to a problem of inspection system. In this case, the largest two grayscales may be defined as the extreme grayscales. In the contrary, if engineers diagnose that the grayscales are deviated to low due to another problem of inspection system, the smallest two grayscales may be defined as the extreme grayscales.

Various statistical process control charts may be employed to assist the error diagnose. The control charts should be carefully used because there may be absence of a target value for the charged particle beam inspection.

Referring to FIG. 1 again, in step 30, a statistic method is employed to determine a nominated grayscale of the pixel from the remained grayscales. Preferably, the remained grayscales are averaged and the average value is used to denote the pixel, i.e., as the nominated grayscale of the pixel. In another embodiment, the median of the remained grayscales is used to denote the pixel. In another embodiment, the nominated grayscale is determined by other statistical methods except the average and median method. In another embodiment, in case of the distribution is abnormal or for other reasons, the remained grayscales may be manipulated through other methods to denote the pixel.

Figure 5:
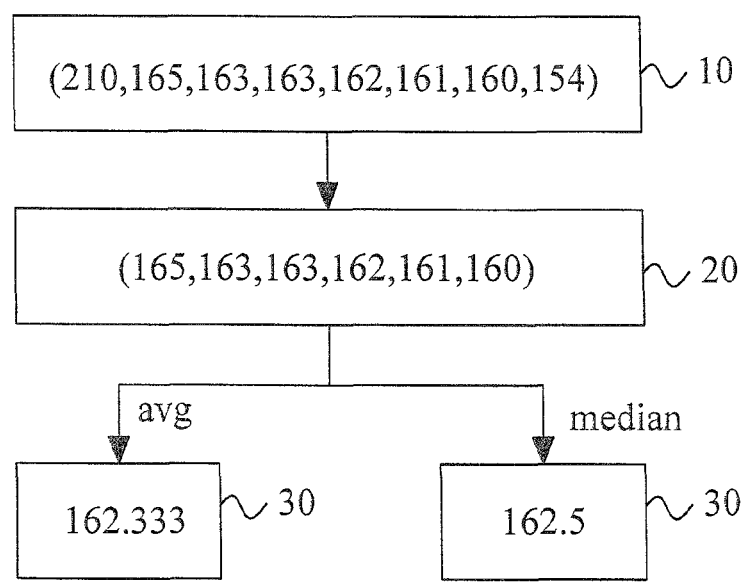
FIG. 5 shows an example of FIG. 1.

FIG. 5 shows an example of FIG. 1. A eight-times scan in time sequence is performed to an extreme ultraviolet mask, and eight grayscales of each pixel are stored in which step 10 shows eight grayscales of a pixel, i.e., 210, 165, 163, 163, 162, 161, 160, and 154. In step 20, the maximum and the minimum grayscale of the eight, i.e., 210 and 154, are automatically removed due to out of the upper and lower limits or for other reasons, and other six grayscales are remained. In step 30, the average or the median of the remained six grayscales is calculated to be the nominated grayscale of the pixel, which is 162.33 for the average or 162.5 for the median.

Another embodiment of this invention provides a system for enhancing image quality, which comprises: means for recording a sequence of grayscales of a pixel scanned by a charged particle beam; means for removing extreme values from the sequence of grayscales and remaining other grayscales of the sequence of grayscales; and means for determining a nominated grayscale of the pixel from the remained grayscales.

The system is configured to store image data generated by scanning a wafer or a mask, such as a silicon wafer or an extreme ultraviolet (EUV) mask. The system may comprises one or more processors coupled to a detector, and each processor receives a portion of image data generated by the detector during scanning. In addition, the system further comprises an array of storage media, such as a memory cell, separately coupled to each processor, storing all of the image data sent by each processor. In addition, the one or more processors may be responsible for removing the extreme values and determining the nominated grayscale, which have been descried in the foregoing paragraphs.

Another embodiment of this invention provides a computer readable medium encoded with a computer program for enhancing image quality of frames obtained from the inspection system. The computer readable medium primarily comprises the steps of: recording a sequence of grayscales of a pixel scanned by a charged particle beam; removing extreme values from the sequence of grayscales and remaining other grayscales; and determining a nominated grey level of the pixel from the remained grayscales.

Figure 6:
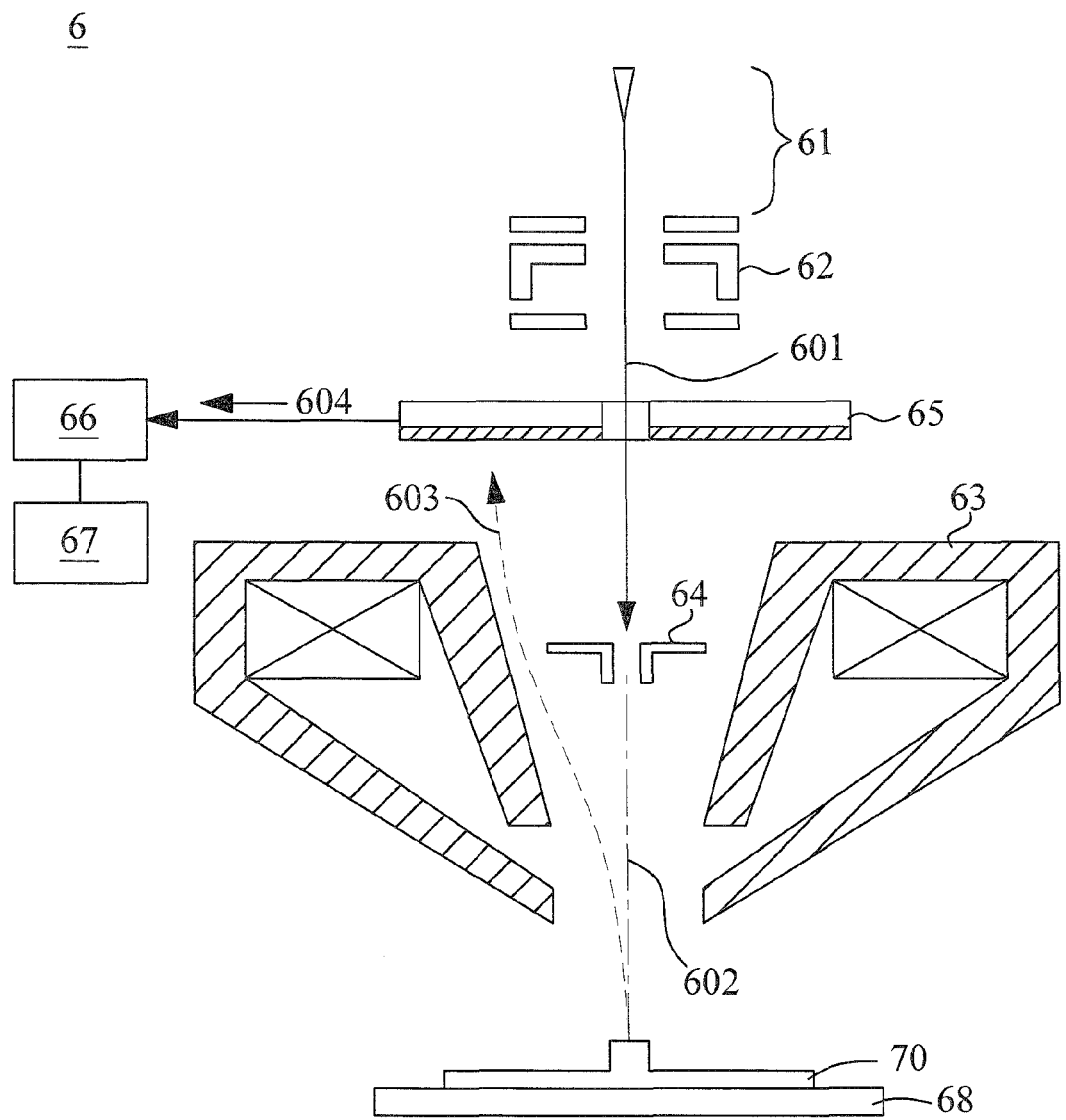
FIG. 6 shows an inspection system 6 according to an embodiment of this invention.

For illustrative purpose, FIG. 6 shows an inspection system 6 according to an embodiment of this invention. A sample 70, such as a wafer or a mask, is loaded on a sample stage 68 to be inspected. A charged particle beam generator 61 generates a primary charged particle beam 601, preferably an electron beam. A condenser lens module 62 condenses the primary charged particle beam 601. A probe forming objective lens module 63 focuses the condensed primary charged particle beam into a charged particle beam probe 602. A charged particle beam deflection module 64 deflects the formed charged particle beam probe 602 to the surface of the sample 70. Secondary charged particles 603 are emitted from the surface of the sample 70 bombarded by the charged particle beam probe 602. A secondary charged particle detector module 65 detects the secondary charged particles 603 and generates a secondary charged particle detection signal 604. An image forming module 66 communicated with the secondary charged particle detector module 65 receives the secondary charged particle detection signal 604 and forms one or more frames. The image forming module 66 may be a host, a terminal, a personal computer, or the like. A noise-filtering module 67 communicated with the image-forming module 66 treats the scanned frames by methods mentioned in the foregoing embodiments, so as to obtain a image with improved quality. noise-filtering module 67 may comprise the above-mentioned processers and memories for storing and processing the image and inspection data of the frames. The connection between the image forming module 66 and the secondary charged particle detector module 65 may be wire or wireless manners known in the art.

Figure 7:
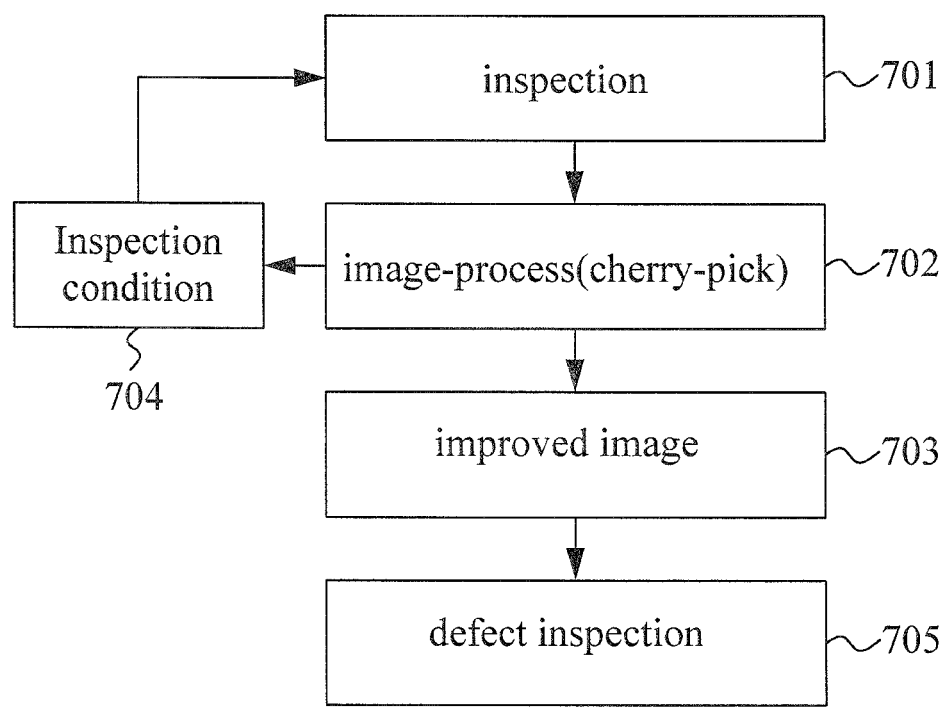
FIG. 7 is a flowchart showing the process of the inspection system according to an embodiment of this invention.

FIG. 7 is a flowchart showing the process of the inspection system according to an embodiment of this invention. Step 701, the inspection system performs a muliti-scan to a sample. Step 702, the results of the multi-scan are treated by the method, particularly the cherry-pick method of this invention. Step 703, after image-processing, an image with improved quality can be obtained. Step 704, in the meantime, the image-processing method analyzes the scanned frames to check the condition of the inspection system. For example, the method may check whether a system error is presented. Step 705, the defects of the sample can be determined by the improved image.

By cherry-picking the recorded sequence of grayscales, each pixel obtains a nominated grayscale with reduced noise. The signal-to-noise ratio of the scanned image is increased and better image quality is hence obtained. The qualified good image quality promotes the accuracy of the alignment process, increase defect-detecting sensitivity, and decrease defect false rate. Accordingly, embodiments of this invention provide methods and system can significantly reduce the inspection time and cost.

Although specific embodiments have been illustrated and described, it will be appreciated by those skilled in the art that various modifications may be made without departing from the scope of the present invention, which is intended to be limited solely by the appended claims.

What is claimed is:

1. A method for enhancing image quality, comprising:
   repeatedly scanning a pixel by a charged particle beam;
   recording a sequence of grayscales of the pixel scanned by the charged particle beam;
   removing extreme values from the sequence of grayscales; and
   determining a nominated grey level of the pixel from remained grayscales in order to enhance the image quality,
   wherein the extreme grayscales of each pixel include less than a lower limit (LL) and more than a upper limit (UL) of grayscales of each pixel, in which the lower limit is $\mu$ minus $0.67\sigma$, the upper limit is $\mu$ plus $0.676\sigma$, and μ and σ respectively stand for the mean and the standard deviation of the grayscales of each pixel.

2. The method of claim 1, wherein the nominated grey level is the average or the median of the remained grayscales.

3. The method of claim 1, wherein the extreme values include the highest 25% and the lowest 25% of the sequence of grayscales.

4. The method of claim 1, wherein the extreme values include the highest 10% and the lowest 10% of the sequence grayscales.

5. The method of claim 1, wherein the sequence is a time mode.

6. The method of claim 5, wherein the charged particle beam is an electron beam.

7. The method of claim 6, wherein the pixel is imaged from a specimen.

8. The method of claim 7, wherein the specimen is an extreme ultraviolet (EUV) mask.

9. The method of claim 7, wherein the specimen is a silicon wafer.

10. A system for enhancing image quality, comprising:
a charged particle beam repeatedly scanning a pixel;
means for recording a sequence of grayscales of the pixel scanned by the charged particle beam;
means for removing extreme values from the sequence of grayscales; and
means for calculating an average or a median of remained grayscales to obtain an nominated grayscale of the pixel in order to enhance the image quality,
wherein the extreme grayscales of each pixel include less than a lower limit (LL) and more than a upper limit (UL) of grayscales of each pixel, in which the lower limit is μ minus 0.67σ, the upper limit is μ plus 0.67σ, and μ and σ respectively stand for the mean and the standard deviation of the grayscales of each pixel.

11. The system of claim 10, wherein the charged particle beam is an electron beam.

12. The system of claim 11, wherein the pixel is imaged from a specimen.

13. The system of claim 12, wherein the specimen is an extreme ultraviolet (EUV) mask.

14. The system of claim 12, wherein the specimen is a silicon wafer.

15. A method for enhancing image quality, comprising:
scanning a specimen to obtain a plurality of frames by using a charged particle beam;
removing extreme grayscales of each pixel of the plurality of frames;
averaging remained grayscales of each pixel of the plurality of frames to obtain a scanned image of the specimen in order to enhance the image quality,
wherein the extreme grayscales of each pixel include less than a lower limit (LL) and more than a upper limit (UL) of grayscales of each pixel, in which the lower limit is μ minus 0.67σ, the upper limit is μ plus 0.67σ, and μ and σ respectively stand for the mean and the standard deviation of the grayscales of each pixel.

16. The method of claim 15, wherein the plurality of frames have a time sequence in the scanning step.

17. The method of claim 16, wherein the charged particle beam is an electron beam.

18. The method of claim 17, wherein the specimen is an extreme ultraviolet (EUV) mask.

19. The method of claim 17, wherein the specimen is a silicon wafer.

20. The method of claim 18, wherein at least two frames from the plurality of frames with most the extreme grayscales in a statistical result are obtained.

21. A non-transitory computer readable medium encoded with a computer program for enhancing image quality of an inspection system, comprising the steps of:
recording a sequence of grayscales of a pixel scanned by a charged particle beam;
removing extreme values from the sequence of grayscales; and
determining a nominated grey level of the pixel from remained grayscales in order to enhance the image quality,
wherein the extreme grayscales of each pixel include less than a lower limit (LL) and more than a upper limit (UL) of grayscales of each pixel, in which the lower limit is μ minus 0.67σ, the upper limit is μ plus 0.67σ, and μ and σ respectively stand for the mean and the standard deviation of the grayscales of each pixel.

22. The computer readable medium of claim 21, wherein the nominated grey level is the average or the median of the remained grayscales.

23. The computer readable medium of claim 21, wherein the extreme values include the highest 25% and the lowest 25% of the sequence of grayscales.

24. The computer readable medium of claim 21, wherein the extreme values include the highest 10% and the lowest 10% of the sequence grayscales.

25. The computer readable medium of claim 21, wherein the sequence is a time mode.

26. The computer readable medium of claim 21, wherein the charged particle beam is an electron beam.

* * * * *